(12) United States Patent
Schiller

(10) Patent No.: US 9,383,278 B1
(45) Date of Patent: Jul. 5, 2016

(54) ELECTRODE TORQUE MEASUREMENT DEVICE

(71) Applicant: Contractors & Industrial Supply Company, Inc., Nashville, TN (US)

(72) Inventor: Tom D. Schiller, Franklin, TN (US)

(73) Assignee: Contractors & Industrial Supply Company, Inc., Nashville, TN (US)

( * ) Notice: Subject to any disclaimer, the term of this patent is extended or adjusted under 35 U.S.C. 154(b) by 0 days.

(21) Appl. No.: 14/693,621

(22) Filed: Apr. 22, 2015

Related U.S. Application Data

(60) Provisional application No. 61/982,337, filed on Apr. 22, 2014.

(51) Int. Cl.
| | |
|---|---|
| *G01B 7/16* | (2006.01) |
| *G01L 5/24* | (2006.01) |
| *G01L 1/20* | (2006.01) |
| *H05B 7/14* | (2006.01) |
| *H05B 7/152* | (2006.01) |
| *G01N 27/28* | (2006.01) |

(52) U.S. Cl.
CPC ... *G01L 5/24* (2013.01); *G01L 1/20* (2013.01); *H05B 7/14* (2013.01); *G01N 27/28* (2013.01); *H05B 7/152* (2013.01); *Y02P 10/259* (2015.11)

(58) Field of Classification Search
CPC ............ G01N 27/28; G01L 5/24; G01L 1/20; Y02P 10/259; H05B 7/14; H05B 7/152
USPC ...................................... 73/760, 774, 862.08
See application file for complete search history.

(56) References Cited

U.S. PATENT DOCUMENTS

| | | | | | |
|---|---|---|---|---|---|
| 3,781,449 | A | * | 12/1973 | Wolf ......................... | H05B 7/12 373/107 |
| 4,665,530 | A | * | 5/1987 | Corbethau ............... | H05B 7/14 373/92 |
| 4,703,492 | A | * | 10/1987 | Sekiguchi ................ | H05B 7/14 373/91 |
| 4,736,384 | A | * | 4/1988 | Sakai ....................... | H05B 7/14 373/92 |
| 5,255,285 | A | * | 10/1993 | Aberl ...................... | F27B 3/085 373/102 |
| 5,638,398 | A | * | 6/1997 | Ikitsu .................... | B23P 19/105 29/705 |
| 5,870,424 | A | * | 2/1999 | Todoriki .................. | H05B 7/14 373/91 |
| 6,167,076 | A | * | 12/2000 | Ignacio .................... | H05B 7/14 373/100 |

* cited by examiner

*Primary Examiner* — Max Noori
(74) *Attorney, Agent, or Firm* — Matthew C. Cox; Waller Lansden Dortch & Davis, LLP

(57) ABSTRACT

An electrode joining apparatus for joining a fixed electrode and a free electrode including an electrode holder configured to receive the fixed electrode and a torque device positioned above the electrode holder. The torque device is configured to grip and spin the free electrode to join the free electrode to the fixed electrode. A force sensor is coupled to the torque device. The torque device is configured to apply a force on the force sensor when the torque device engages the free electrode, the force sensor configured to detect a signal representative of the force applied by the torque device on the free electrode. The feedback force signal can be used to determine the torque applied to the free electrode by the torque device to help ensure that a proper joint is formed between the free electrode and the fixed electrode.

20 Claims, 11 Drawing Sheets

ELECTRODE TORQUE MEASUREMENT DEVICE

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

This application is a non-provisional of U.S. Provisional Patent Application Ser. No. 61/982,337 filed Apr. 22, 2014 entitled Electrode Joining Apparatus And Methods, which is herein incorporated by reference in its entirety.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present invention relates generally to machinery for manipulating electrodes and more particularly to devices and methods for joining graphite electrodes for use with metal arc furnaces.

Metal arc furnaces include large vessels for melting metal. Heat may be generated inside the furnaces using graphite electrodes across which electric current is passed. Heat is generated inside the furnace due to a high voltage arc formed by the current passing through one or more electrodes. The heat is used to melt metal.

During use, graphite electrodes are consumed within the furnace vessel, requiring electrodes to be replaced over time. As electrode material is consumed in the furnace, the electrode is shortened to a length where it is no longer independently usable. However, a partially-consumed electrode may be joined to a second partially-consumed or complete electrode to form a joined electrode that can be used. Thus, the partially-consumed electrode may still be useful when placed in combination with a second electrode portion.

Electrodes may be joined in an end-to-end configuration using a threaded joint in some applications. When electrodes are combined, electrical conductivity is generally maintained across the joint, and electricity may be passed from one electrode to the second in the joint electrode. A threaded joint is commonly used to join electrodes. The joining procedure requires at least one electrode to be rotated relative to a second electrode such that a threaded engagement occurs.

The joining process typically requires two stages. During a first stage, the first electrode is rotated relative to the second electrode to allow loose engagement of the corresponding threads. Rotation during this stage encounters relatively little resistance as the threads are rotating. This may be referred to as a spin-down rotation when a free electrode is spun about its longitudinal axis relative to a fixed electrode below the free electrode, to allow the threads to engage.

Before use, the threaded electrode joint must be tightened to a predetermined manufacturer's suggested torque value. A second stage of electrode joining occurs when the end walls of the two electrodes or other structures make contact, requiring greater force to torque the first electrode relative to the second electrode. During this stage, the torque applied generally increases as a function of angular position. This second stage may be referred to as a torque stage. Once a desired torque value, or a value within a desired torque range, is reached, force application is ceased and the electrodes are properly joined.

An improper torque application can damage threads, reduce electrical connectivity between the electrode sections, or cause failure of the joint. Such failure may be catastrophic where the separate electrode sections each weigh several hundred or even several thousand pounds. Because joined electrodes are typically moved inside an industrial setting using overhead transport rigging, joint failure can cause one or both electrode sections to crash down on equipment or workers, causing major damage or injury.

Conventional tools and methods for joining electrodes in a threaded joint include manually rotating one free electrode relative to a fixed electrode. This may be achieved using a manual wrench or other tool for grasping and rotating the free electrode. The applied torque may be measured manually using a torque gauge or manual torque wrench. The conventional manual joining technique is time-consuming for workers and may be dangerous in some applications due to the requirement that a worker be near the additional electrode operating the wrench. Additionally, manual procedures lead to variance in applied torque values as workers may not apply the same torque every time.

Others have attempted to solve the problems associated with manual joining of threaded electrodes by providing devices to assist in the torque application process. For example, U.S. Pat. No. 6,167,076 titled Electrode Wrench provides an apparatus for joining a threaded free electrode section with a threaded fixed electrode section for use in electric arc furnaces. The apparatus includes a driver and a plurality of pawls to grip the free electrode and turn it in one angular direction. The electrode wrench includes a pneumatic cylinder to apply torque against the free electrode in the second stage of joining. During use, a user may measure the pressure applied in the pneumatic cylinder and correlate the pressure to a range of torque values. Thus, a user may stop applying force once a pressure value corresponding to a desired torque range is reached. However, the electrode wrench typically does not provide independent verification, or feedback measurement of applied torque. The failure of such independent verification can lead to improper torque application on the free electrode and the undesirable and dangerous problems mentioned above.

What is needed then are electrode joining apparatuses with improved feedback torque detection.

SUMMARY OF THE INVENTION

One aspect of the present disclosure is an electrode joining apparatus for joining a fixed electrode and a free electrode including an electrode holder configured to receive the fixed electrode and a torque device positioned above the electrode holder. The torque device is configured to grip and spin the free electrode to join the free electrode to the fixed electrode. A force sensor is coupled to the torque device. The torque device is configured to apply a force on the force sensor when the torque device engages the free electrode, the force sensor configured to detect a signal representative of the force applied by the torque device on the free electrode. The feedback force signal can be used to calculate the torque applied to the free electrode by the torque device to help ensure the proper amount of torque is applied to the free electrode.

In some embodiments, the electrode joining apparatus can also include an input indicator. The input indicator can show the value of an input for the torque device such as a hydraulic or pneumatic pressure which is being supplied to a drive motor of a torque device. The input pressure can be correlated to a torque value to determine the amount of torque being supplied to the free electrode. As such, the electrode joining device can include two verification methods for determining the torque applied to the free electrode.

Another aspect of the present disclosure is an electrode torque measurement apparatus for an electrode joining device, the electrode joining device including an electrode holder configured to receive a fixed electrode, and a torque device configured to grip and spin a free electrode to join the free electrode to the fixed electrode. The apparatus includes a base ring mountable to the electrode joining device and a drive ring mountable to the torque device, the drive ring rotatable relative to the base ring. A force sensor can be coupled between the base ring and the drive ring. The torque device can be configured to apply a force on the force sensor via the drive ring when the base ring is mounted to the electrode joining device, the drive ring is mounted to the torque device, and the torque device engages the free electrode, the force sensor configured to detect a signal representative of the force applied by the torque device on the free electrode. Such an apparatus can be retrofitted to existing electrode joining devices to help provide a feedback torque measurement of an applied torque on a free electrode by a torque device.

One objective of the present disclosure is to provide feedback detection of an applied torque force on a free electrode in an electrode joining apparatus.

Another objective is to accurately determine the amount of torque being applied to a free electrode being joined to a fixed electrode in an electrode joining apparatus.

Numerous other objects, advantages and features of the present disclosure will be readily apparent to those of skill in the art upon a review of the following drawings and description of a preferred embodiment.

DETAILED DESCRIPTION

Figure 1:
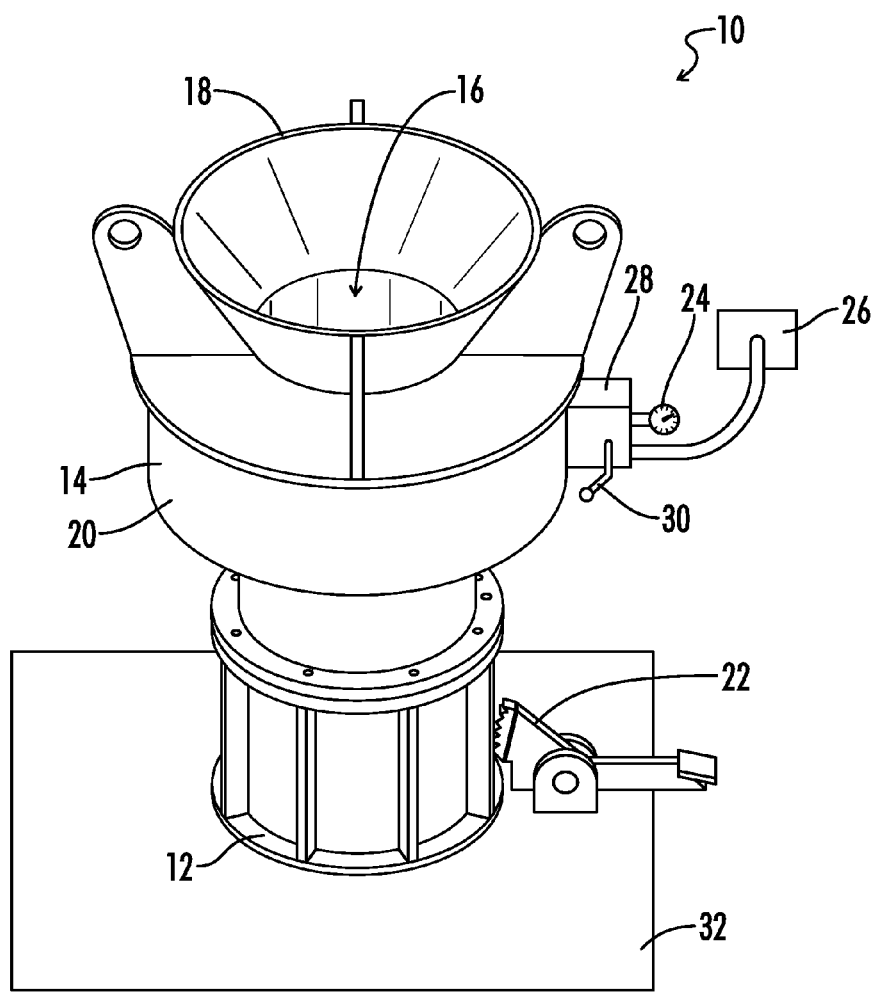
FIG. 1 is a perspective view of an embodiment of an electrode joining apparatus with an electrode holder and a torque device.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention.

To facilitate the understanding of the embodiments described herein, a number of terms are defined below. The terms defined herein have meanings as commonly understood by a person of ordinary skill in the areas relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims.

As described herein, an upright position is considered to be the position of apparatus components while in proper operation or in a natural resting position as described herein. Vertical, horizontal, above, below, side, top, bottom and other orientation terms are described with respect to this upright position during operation unless otherwise specified. The term "when" is used to specify orientation for relative positions of components, not as a temporal limitation of the claims or apparatus described and claimed herein unless otherwise specified. The term "lateral" denotes a side to side direction when facing the "front" of an object.

The phrase "in one embodiment," as used herein does not necessarily refer to the same embodiment, although it may. Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the apparatuses and/or methods disclosed and claimed herein may be made and/or executed without undue experimentation in light of the present disclosure. While the apparatuses and methods of this invention have been described in terms of the embodiments included herein, it will be apparent to those of ordinary skill in the art that variations may be applied to the apparatuses and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Referring now to the drawings, an embodiment of an electrode joining apparatus 10 is shown in FIG. 1. Electrode joining apparatus 10 can include electrode holder 12 and torque device 14. An axial passage 16 can extend through electrode holder 12 and torque device 14, axial passage 16 allowing passage of one or more electrodes through electrode joining apparatus 10. In some embodiments, torque device 14 can include an upper funnel 18 which can facilitate centering of an electrode being lowered into electrode joining apparatus 10 through axial passage 16.

In some applications, graphite electrodes can be joined in an end to end fashion using a threaded joint. Joining the electrodes requires one electrode to be rotated relative to the other electrode. In such applications, a fixed electrode can be received and selectively held by electrode holder 12 and torque device 14 can be configured to grip and spin a free electrode down onto the fixed electrode to effectively join the two electrodes together. Electrode holder 12 can include a holder grip 22 which can be rotated to selectively fix or clamp an electrode within electrode holder 12. In some embodiments, electrode holder 12 can be configured to prevent rotational or axial movement of an electrode once the holder grip 22 engages the electrode. Electrode holder 12 can be securely fixed to a platform 32 on which operators can work. As such, in some embodiments, electrode holder 12 can be rotationally fixed to platform 32.

When joining two electrodes, it is desirable to tighten the electrodes to certain manufacturer recommended torque values. For instance, in some applications, depending on the size of the electrodes, manufacturer recommended torque values can fall between 600 and 10,000 foot-pounds of torque. Tightening the electrodes to the proper torque value can help ensure a proper joint is formed between the electrodes which can help reduce joint failure as well as other potentially dangerous conditions. Improper torque application can cause thread damage or joint failure, which could cause serious injury or damage in an industrial setting with workers nearby. An improperly torqued electrode joint could also affect electrical connectivity between the two electrodes which could adversely affect the efficiency of the furnace.

In some embodiments, torque device 14 can include machinery which can rotate a free electrode lowered through funnel 18 into torque device 14. The machinery can be contained in housing 20. The machinery can generally grip the lower end of the free electrode and apply a rotational force to the free electrode. The machinery can apply rotational force to the free electrode during both the spin down and torque stages, or in some embodiments the machinery can be configured to apply rotational force to the free electrode only during the torque stage. In some embodiments, the machinery can be powered by a mechanical actuator 26 such as a hydraulic pressure system, or a pneumatic pressure system. In other embodiments the machinery can be powered electrically or manually.

In some embodiments, electrode joining apparatus can include an input indicator 24 which can measure a desired value of the input source. For instance in FIG. 1, torque device 14 can be configured to receive a hydraulic input from a hydraulic pump 26, and input indicator 24 can be a hydraulic pressure gauge configured to measure the pressure from hydraulic pump 26 being supplied to the torque device machinery. In other embodiments, torque device 14 can be configured to receive a pneumatic input, and the input indicator 24 can be a pneumatic pressure gauge configured to measure the pneumatic pressure being supplied to the torque device machinery.

In some embodiments, torque device 14 can include a control console 28 including a lever 30 which can be used to supply hydraulic or pneumatic pressure to the machinery. The operator can use input indicator 24 to correlate an indicated pressure with a corresponding torque value. As additional hydraulic or pneumatic pressure is supplied to torque device 14, input indicator 24 will show the rise in pressure accordingly. When the pressure reaches a desired amount which correlates to a desired torque or torque range, the operator can stop applying additional input pressure.

In other embodiments, control console 28 can be mounted to torque device 14. In other embodiments, control console 28 can be placed in a separate location such as a control room or other remote location and torque device 14 can be operated without an operator being present near electrode joining apparatus 10. In some embodiments, control console 28 can be electrically connected to torque device 14, while in other embodiments control console 28 can communicate with torque device 14 through wireless telemetry.

While such a system can be helpful to produce an electrode torque application, the accuracy of the torque being applied to the free electrode depends heavily on the accuracy of the calibrated correlation between the input pressure and the applied torque on the free electrode. If the calibration is incorrect, the accuracy of the determined torque application can be negatively affected. Additionally, correlating an input pressure to an applied torque force does not take into account any losses or inefficiencies in the torque device machinery. If there are any inefficiencies in the system then the actual torque applied may in reality be less than the determined or correlated torque value, which could lead to improper joining of the electrodes.

Figure 2:
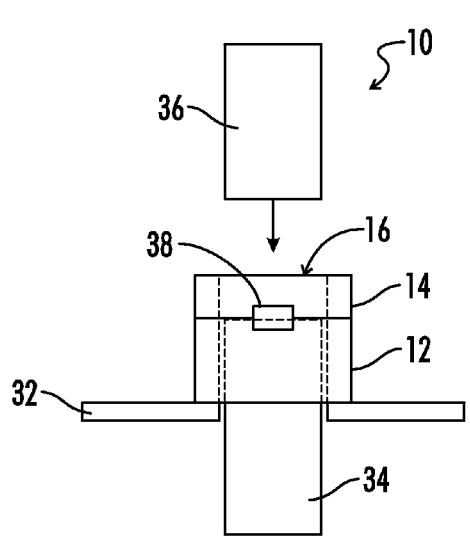
FIG. 2 is a front elevation view of an embodiment of an electrode joining apparatus with a force sensor.

In some embodiments, electrode joining apparatus 10 can include an applied torque feedback detection feature. The applied torque feedback detection feature can help verify or corroborate the determined or calibrated torque value from input indicator 24. As shown in FIG. 2, electrode holder 12 can receive a fixed electrode 34, and a free electrode 36 can be lowered into axial passage 16 such that torque device 14 can engage free electrode 36. A force sensor 38 can be coupled to torque device 14. Torque device 14 can be configured to apply a force on force sensor 38 when torque device 14 engages free electrode 36. Force sensor 38 can be configured to detect a signal representative of the force applied by torque device 14 on free electrode 36. The force applied by torque device 14 on force sensor 38 can be equivalent to the force applied by torque device 14 on free electrode 36. The force detected by force sensor 38 can then be multiplied by the radial distance from the axial center of electrode joining apparatus 10 to force sensor 38 in order to determine the torque being applied to free electrode 36 by torque device 14. In some embodiments, torque device 14 can be configured to apply a compressive force on force sensor 38. In other embodiments, torque device 14 can be configured to apply a tension force on force sensor 38.

In some embodiments, electrode joining apparatus 10 can be an off-furnace type electrode joining apparatus 10, with fixed electrode 34 being removed from a furnace and placed in electrode joining apparatus 10 which is separated from the furnace. In other embodiments, electrode joining apparatus 10 can be an on-furnace type electrode joining apparatus 10, where a free electrode 36 is joined to a fixed electrode 34 while fixed electrode 34 is still disposed in the furnace.

In conventional electrode joining devices, a torque device 14 is typically bolted or securely fastened to an electrode holder 12 or other rotationally fixed component of electrode joining apparatus 10, as shown in FIG. 1. Torque device 14 is typically bolted to electrode holder 12 so that torque device 14 does not move during the joining operation. As such, a force from torque device 14 could not be directly detected because the torque device 14 was not free to move with respect to electrode holder 12. However, in embodiments including a torque feedback detection feature, as shown in FIG. 2, torque device 14 can be rotatable relative to electrode holder 12. As such, as torque device 14 is operated, torque device 14 will be inclined to rotate. Force sensor 38 can be configured to resist the rotation of torque device 14 in order to detect the force applied by torque device 14 on force sensor 38. As such, while torque device 14 can be rotatable relative to electrode holder 12, force sensor 38 can effectively prevent the rotation of torque device 14 such that torque device 14 does not actually rotate during operation.

Figure 3:
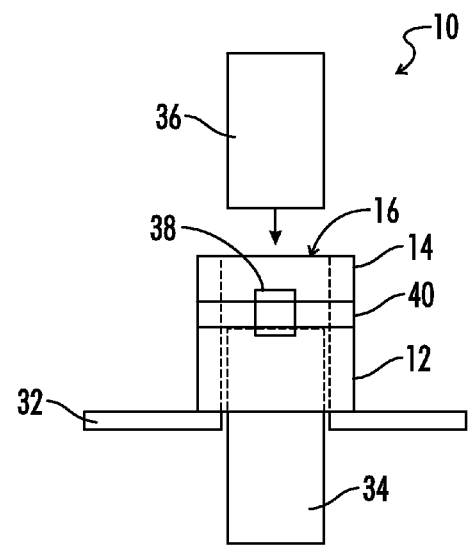
FIG. 3 is a front elevation view of an embodiment of an electrode joining apparatus with an intermediate ring positioned between the electrode holder and the torque device.

In some embodiments, force sensor 38 can be coupled to torque device 14 and electrode holder 12, as shown in FIG. 2. In other embodiments, as shown in FIG. 3, electrode joining apparatus 10 can include an intermediate ring or flange 40 positioned between electrode holder 12 and torque device 14. In some embodiments, intermediate ring 40 can be rotatable with respect to electrode holder 12 and intermediate ring 40 can be mounted to torque device 14 such that torque device 14 is rotatable relative to electrode holder 12 via intermediate ring 40.

In such embodiments, force sensor 38 can be coupled to torque device 14 and electrode holder 12. In other embodiments, force sensor 38 can be coupled to torque device 14 via intermediate ring 40. When force sensor 38 is coupled to torque device 14 via intermediate ring 40, torque device 14 can be configured to apply a force on force sensor 38 via intermediate ring 40.

Figure 4:
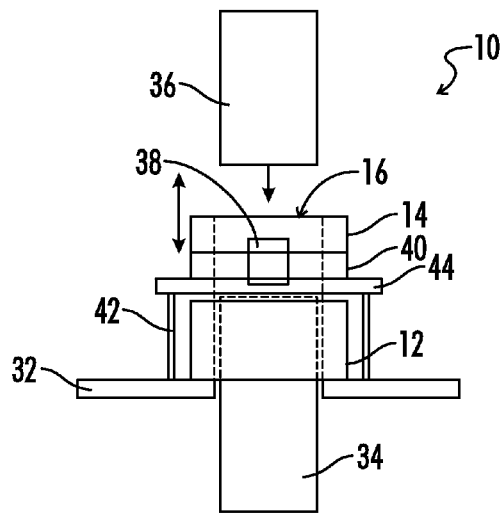
FIG. 4 is a front elevation view of an embodiment of an electrode joining apparatus including a lift that can vary the vertical position of the torque device.

In still other embodiments, electrode joining apparatus 10 can include a lift 42, as shown in FIG. 4. Lift 42 can be configured to vary the vertical position of torque device 14. In some electrode joining procedures, when a fixed electrode 34 is lowered into electrode joining apparatus 10, the dimensions of an electrode carrier on a crane may limit the distance fixed electrode 34 can be lowered into electrode joining apparatus 10 such that the top of fixed electrode 34 is positioned above torque device 14. It may then be necessary to raise torque device 14 such that torque device 14 can engage a free electrode 36 positioned above fixed electrode 34.

Lift 42 may include carriage 44 which torque device 14 can be positioned on. Lift 42 then moves carriage 44 vertically to vary the position of torque device 14 as necessary. Lift 42 can include any suitable mechanism for lifting torque device 14 via carriage 44, including a hydraulic, pneumatic, or electric lift mechanism. In embodiments including a lift 42, force sensor 38 can be coupled to torque device 14 and carriage 44 of lift 42, as shown in FIG. 4 such that torque device 14 is configured to apply a force on force sensor 38 when torque device 14 engages free electrode 36. In some embodiments, torque device 14 can be rotatable relative to carriage 44 such that force sensor 38 resists the rotation of torque device 14 on carriage 44. Additionally, in some embodiments, electrode joining apparatus 10 can include intermediate ring 40 positioned between torque device 14 and carriage 44, intermediate ring 40 being rotatable relative to carriage 44. In some embodiments, force sensor 38 can be coupled to torque device 14 via intermediate ring 40.

Another aspect of the present disclosure is an electrode torque measurement apparatus for an electrode joining device. Electrode torque measurement apparatus 50, shown in FIG. 5, can be used to retrofit existing electrode joining devices with a torque feedback detection system. Electrode torque measurement apparatus 50 can include a base ring 52 mountable to an electrode joining apparatus. In some embodiments, base ring 52 is mountable to an electrode holder of an electrode joining device. In other embodiments where the electrode joining device includes a lift, base ring 52 can be mountable to a carriage of the lift.

Figure 5:
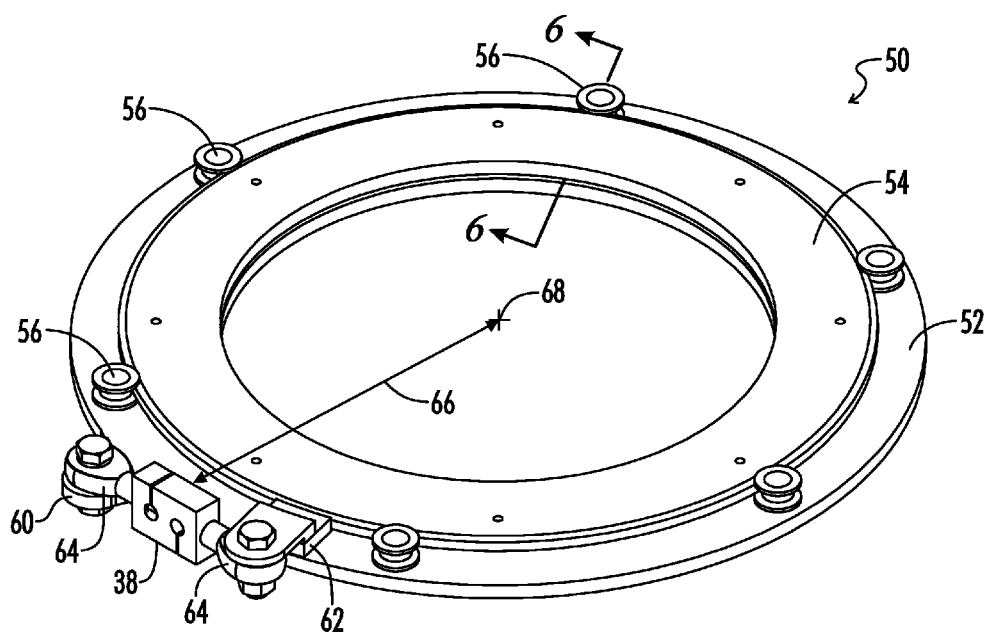
FIG. 5 is a perspective view of an embodiment of an electrode torque measurement apparatus for an electrode joining device.
Figure 6:
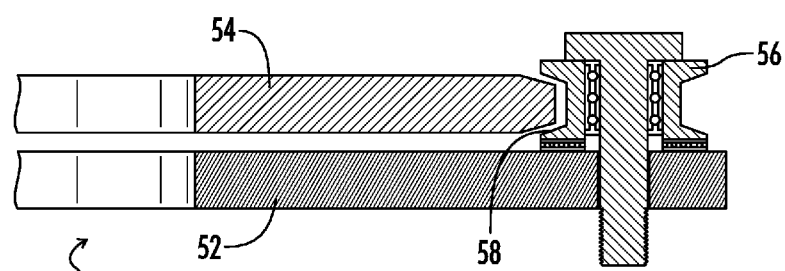
FIG. 6 is a partial cross section view of the electrode torque measurement apparatus of FIG. 5.

Electrode torque measurement device 50 can include a drive ring 54 mountable to a torque device of the electrode joining apparatus. Drive ring 54 can be rotatable relative to base ring 52. As can be seen in FIGS. 5 and 6, electrode torque measurement apparatus 50 can include a plurality of rollers 56 disposed on base ring 52. The plurality of rollers 56 can be positioned to accommodate drive ring 54 such that drive ring 54 is rotatable relative to base ring 52. In some embodiments, each of the plurality of rollers 56 has a beveled load-bearing surface 58 which can accommodate and support drive ring 54. A force sensor 38 can be coupled to base ring 52 and drive ring 54. In some embodiments, base flange 60 can extend radially from base ring 52. Force sensor 38 can then be coupled to base ring 52 via base flange 60. In some embodiments, drive flange 62 can extend radially from drive ring 54. Force sensor 38 can then be coupled to drive ring 54 via drive flange 62. Force sensor 38 can include two load rods 64 which can be coupled to the base flange 60 and the drive flange 62 respectively.

Figure 7:
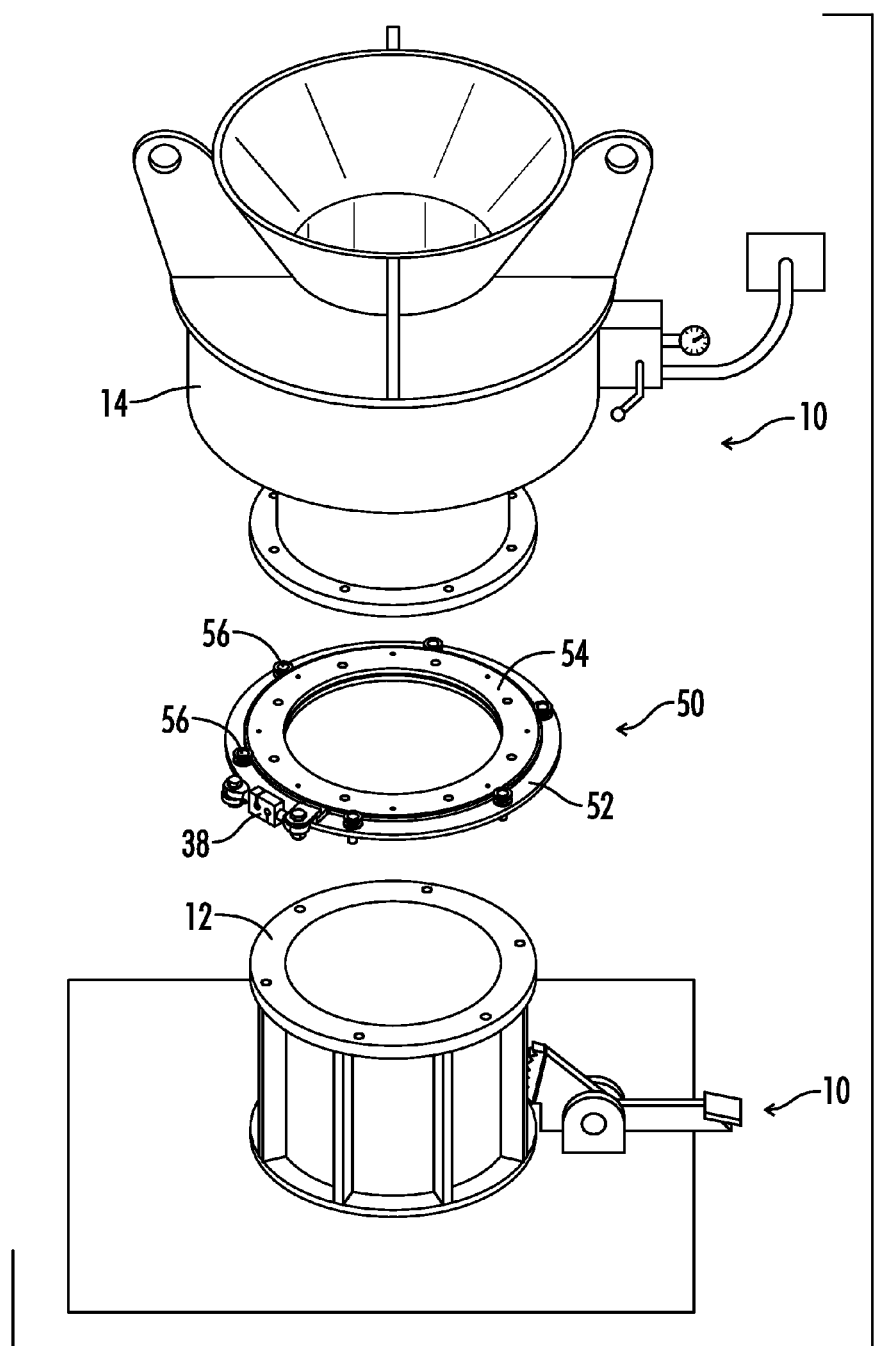
FIG. 7 is an exploded view of an embodiment of an electrode joining apparatus including the electrode torque measurement apparatus of FIG. 5.
Figure 8A:
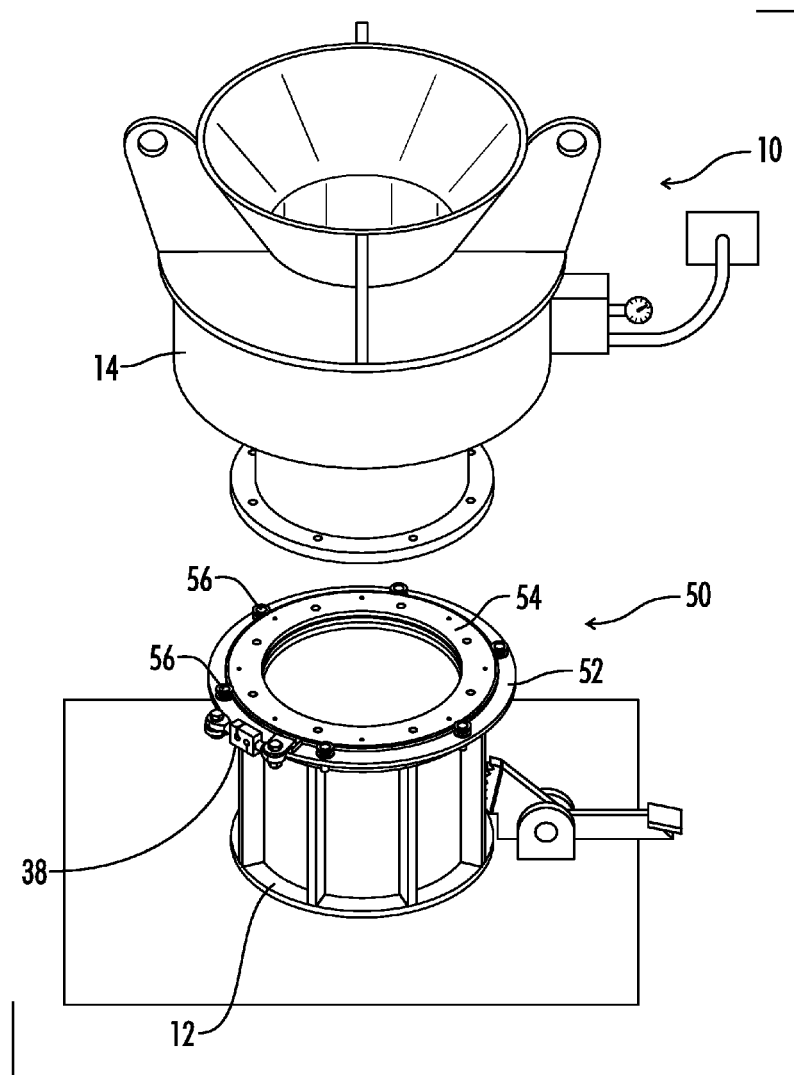
FIG. 8A is a partial exploded view of the electrode joining apparatus of FIG. 7.
Figure 8B:
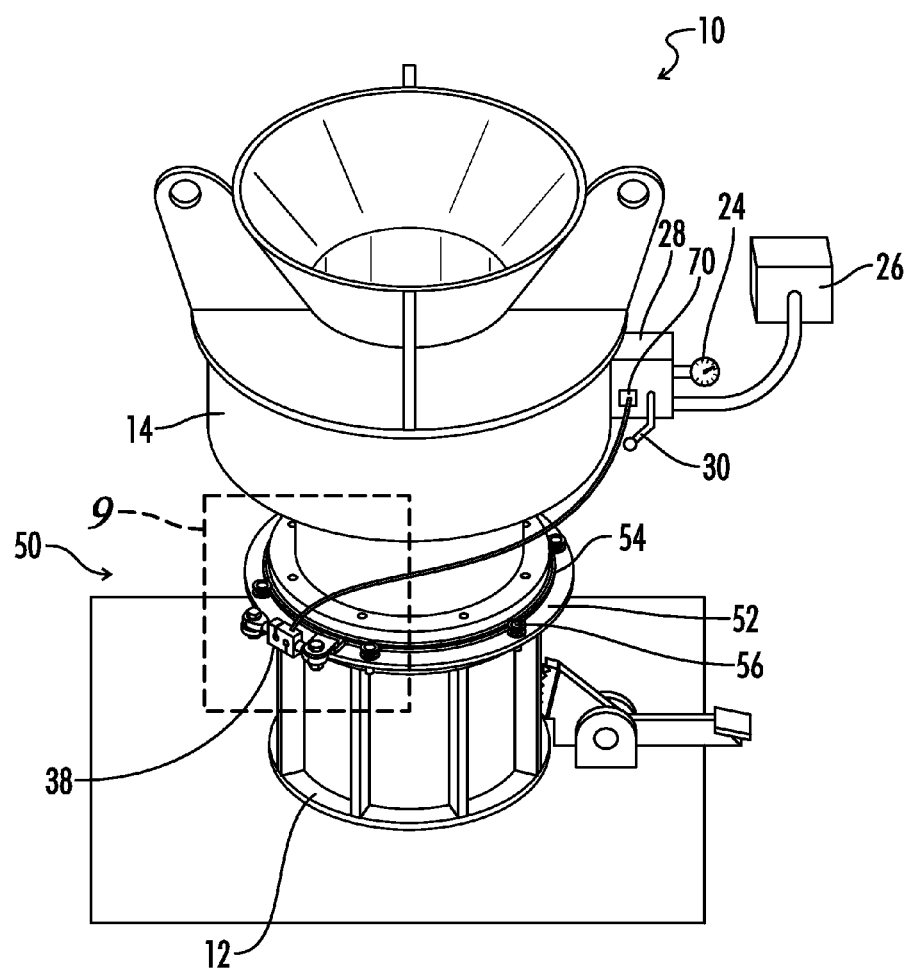
FIG. 8B is an assembled perspective view of the electrode joining apparatus of FIG. 7.

FIG. 7 shows an exploded view of electrode torque measurement apparatus 50 of FIG. 5 being integrated into electrode joining apparatus 10 of FIG. 1. Electrode holder 12 and torque device 14 can be unbolted from each other, and electrode torque measurement apparatus 50 can be positioned between electrode holder 12 and torque device 14. FIG. 8A shows a partially assembled view with base ring 52 being mounted to electrode holder 12, and FIG. 8B shows a fully assembled view of electrode joining apparatus 10 including electrode torque measurement apparatus 50, with drive ring 54 being mounted to torque device 14.

In those electrode joining devices including a lift for varying the vertical position of a torque device above an electrode holder, the torque device can be detached from a carriage of the lift, and electrode torque measurement apparatus 50 can be positioned between the torque device and the carriage. Base ring 52 can similarly be mounted to the carriage and drive ring 54 can be mounted to the torque device to incorporate the electrode torque measurement apparatus 50 with the electrode joining apparatus having a lift.

Figure 9:
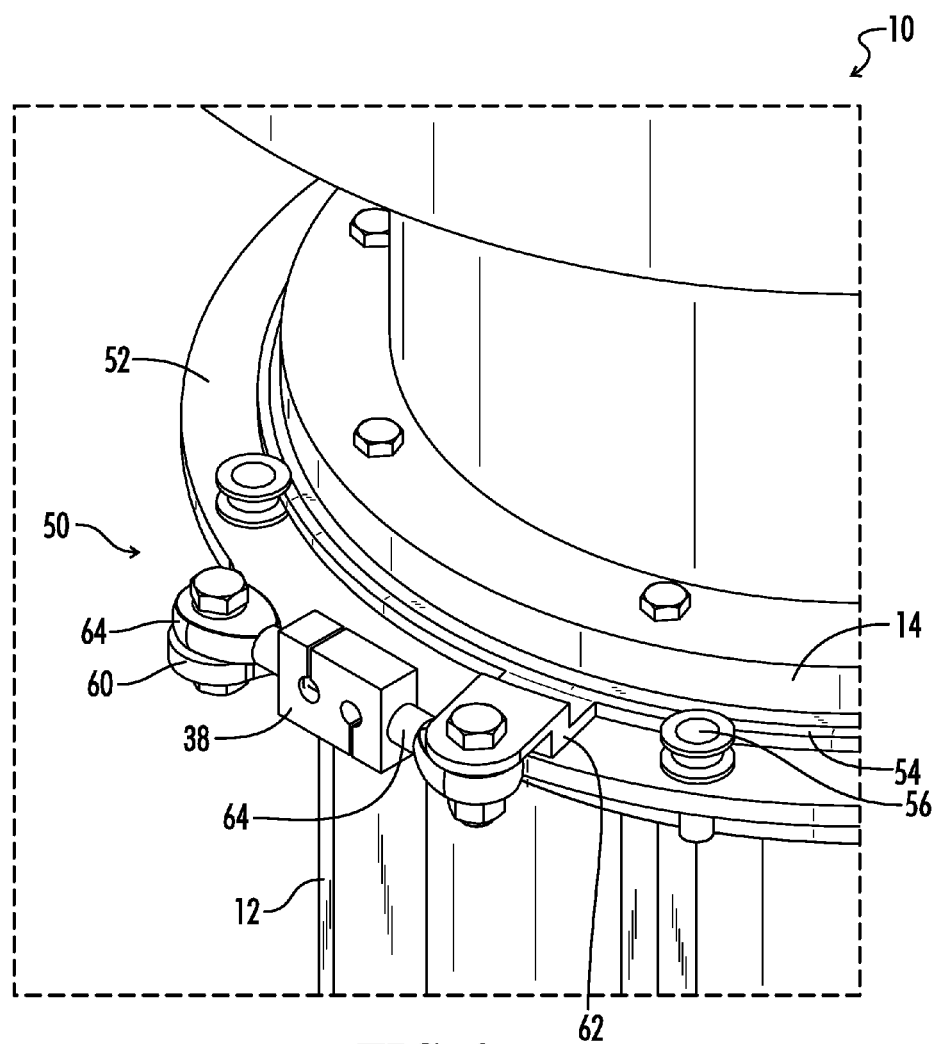
FIG. 9 is a detailed perspective view of the electrode joining apparatus of FIG. 8B.

Referring now to FIG. 9, with electrode torque measurement apparatus 50 mounted to electrode joining apparatus 10, torque device 14 can be rotatable relative to electrode holder 12. As torque device 14 engages a free electrode, torque device 14 and drive ring 54 will be inclined to rotate on base ring 52 and rollers 56, thereby producing a force on force sensor 38. Force sensor 38 can resist the rotation of drive ring 54 and torque device 14 in order to detect the force being applied on force sensor 38 by torque device 14. The force on force sensor 38 can be representative of the force applied by torque device 14 on the free electrode.

Figure 10:
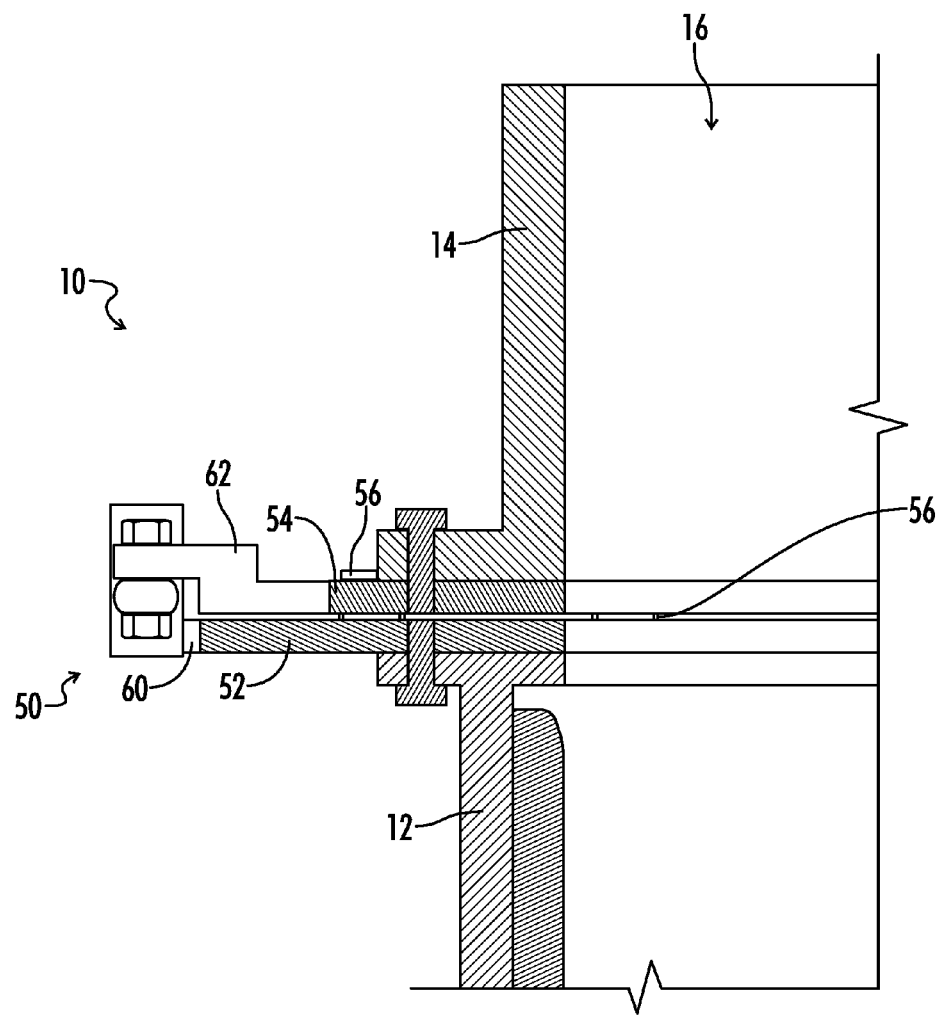
FIG. 10 is a partial cross section view of the electrode joining apparatus of FIG. 8B.

As shown in FIG. 10, in some embodiments, base ring 52 and drive ring 54 can be configured to mount to electrode holder 12 and torque device 14 respectively through bolt holes manufactured into electrode holder 12 and torque device 14. As such, electrode torque measuring apparatus 50 can be mounted to electrode joining apparatus 10 without having to substantially alter electrode holder 12 or torque device 14.

Figure 11:
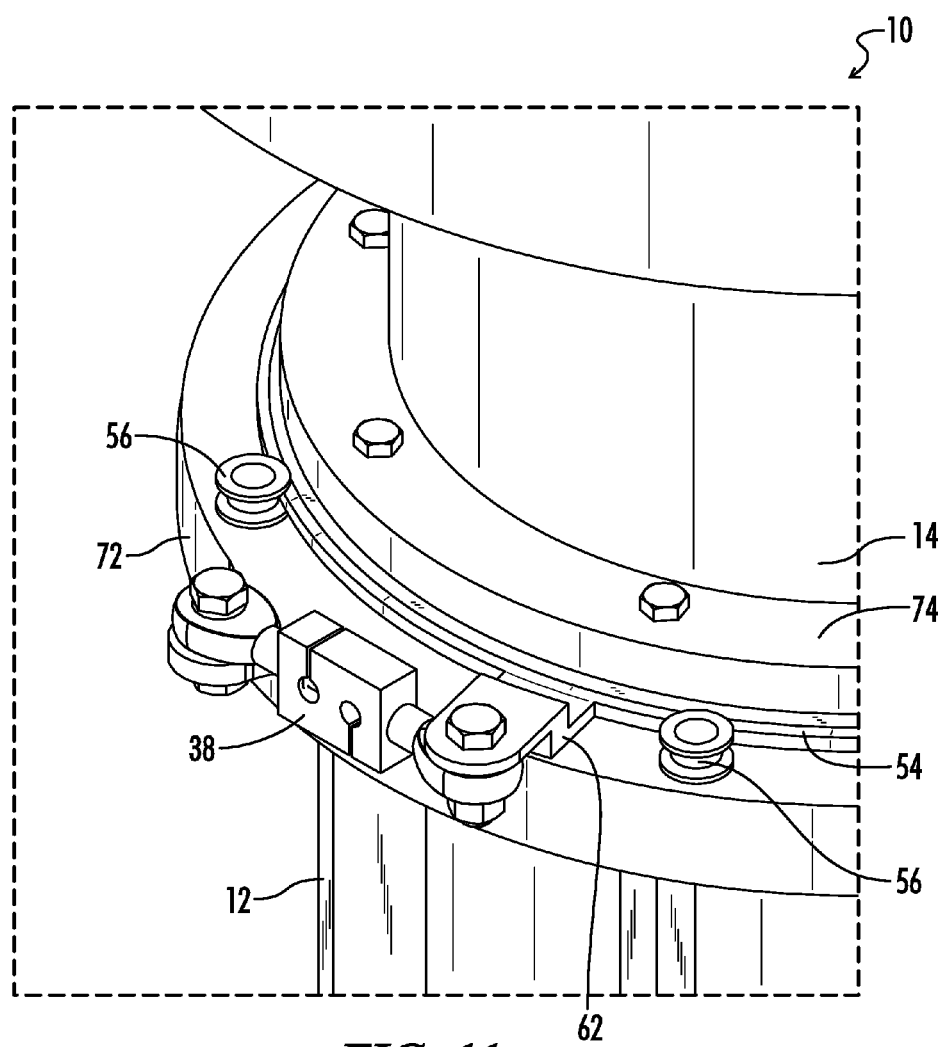
FIG. 11 is a detailed perspective view of another embodiment of an electrode joining device include an force sensor feedback.
Figure 12:
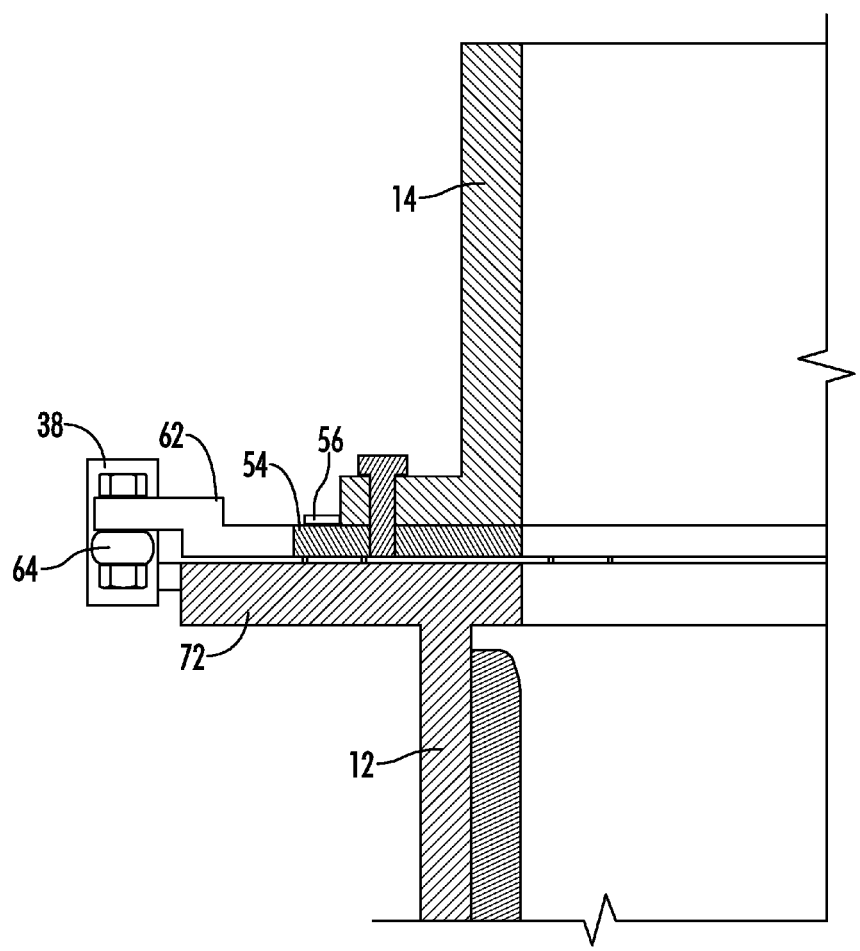
FIG. 12 is a partial cross section view of electrode joining apparatus of FIG. 11.

While FIGS. 7-10 are directed to retrofitting electrode joining devices with electrode torque measuring apparatuses, an electrode joining apparatus 10 can also be manufactured to include many of the features of the electrode measuring apparatus 50 shown in FIG. 5. For instance, in FIG. 11-12, an electrode holder 12 can be manufactured to include a top flange 72 that is wider than a lower flange 74 of a torque device 14. As such, a plurality of rollers 56 can be disposed directly on electrode holder 12. Drive ring 54 attached to torque device 14 could therefore be accommodated in the rollers 56 on electrode holder 12 without the need for an intermediate base ring between electrode holder 12 and drive ring 54. In other embodiments, rollers 56 on top flange 72 of electrode holder 12 could be configured to accommodate lower flange 74 of torque device 14 directly. As such, torque device 14 could be rotatable relative to electrode holder 12 without the need for any intermediate rings. Additionally, force sensor 38 could be coupled directly to either electrode holder 12 or torque device 20, or both, which further alleviates the need for intermediate rings.

Referring again to FIG. 8B, force sensor 38 can be any suitable sensor known in the art that can be configured to detect a signal representative of a load being applied upon force sensor 38. In some embodiments, force sensor 38 can be a load cell. Load cell 38 in some embodiments can have a capacity of greater than or equal to 10,000 pounds. Load cell 38 can have any number of suitable orientations, including but not limited to, an s-shaped configuration. Load cell 38 can include one or more strain gauges, the strain gauges configured to detect the strain deformation of load cell 38 when a force is applied to load cell 38. The strain deformation can then be correlated to an applied force necessary to cause such a deformation in order to determine the force applied on load cell 38.

Load cell 38 can include a transducer which can convert the deformation in load cell 38 into an electronic voltage signal which can be proportional to the force being applied on load cell 38. Load cell 38 can produce either an analog or digital signal. Load cell 38 can also include a filter to reduce undesirable noise in the signal. Load cell 38 can be configured to run on either alternating or direct current, with power being supplied by a separate power source, or power being supplied from control console 28. In one embodiment, load cell 38 can run on 110 volts alternating current.

Referring again to FIG. 5, when electrode torque measurement apparatus 50 is mounted to an electrode joining apparatus, drive ring 54 and base ring 52 can be positioned concentrically with respect to an axial passage of the electrode joining apparatus. As such, the radial distance from the center of the electrode joining apparatus to load cell 38 is equivalent to the distance 66 from the center 68 of drive ring 54 or base ring 52 to load cell 38. As such, as a torque device exerts a force on load cell 38 via drive ring 54, load cell 38 can be configured or programmed to multiply the detected force by the distance 66 to calculate the torque applied on a free electrode by the torque device.

In some embodiments, electrode joining apparatus 10 includes only an applied force sensor 38 to detect an applied torque from torque device 14 on a free electrode. In other embodiments, as shown in FIG. 8B, electrode joining apparatus 10 can include both an applied force sensor 38 and an input indicator 24. As such, the torque applied to a free electrode during the joining operation by torque device 14 can be verified using two different methods as described above, independent of one another, to ensure an accurate torque is applied to the free electrode. The use of both verification methods can help prevent improper joining of electrodes and the problems associated therewith.

In some embodiments, force sensor 38 can be configured to produce a digital display of the calculated torque measurement on or near force sensor 38. In other embodiments, as shown in FIG. 8B, the electric voltage signal output produced by the force sensor 38 can be communicated with control console 28 and a digital display 70 can be produced directly on control console 28. In some embodiments, force sensor 38 is electrically connected to control console 28 in order to communicated the electric voltage signal. In other embodiments, force sensor 38 can be configured to communicated with control console 28 through wireless telemetry. As such, input indicator 24, digital display 70 for applied force sensor 38, and lever 30 to control torque device 14 can all be located on control console 28 so that an operator can operate torque device 14 and verify the torque being applied to a free electrode from the same location.

Figure 13:
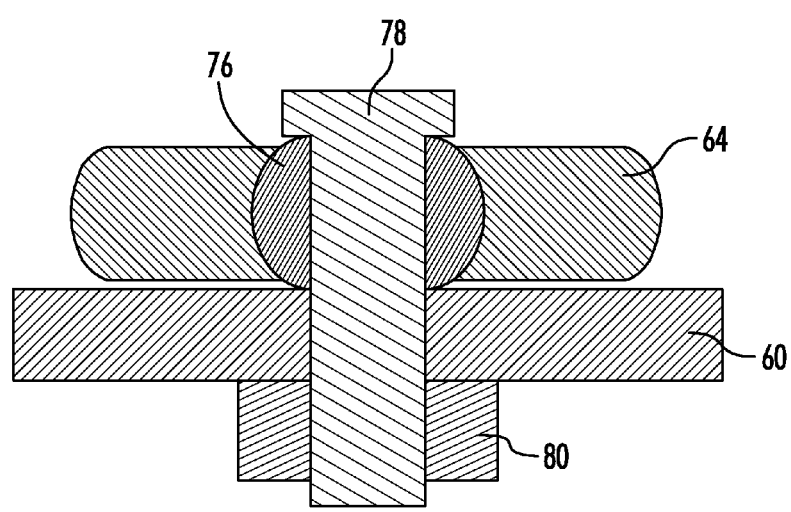
FIG. 13 is a cross section view of a ball joint connection between a load rod of a force sensor and a base flange of FIG. 5.

A cross section of a coupling of a load rod 64 to base flange 60 of FIG. 5 is shown in FIG. 13. The coupling between load rod 64 and base flange 60 can be a ball joint in some embodiments. The ball joint can include a ball bearing 76 disposed within load rod 64, ball bearing 76 having a thickness slightly larger than the thickness of load rod 64. A bolt 78 can extend through ball bearing 76 and base flange 60, and ball bearing 76 and base flange 60 can be clamp together via a nut 80 rotated onto a threaded end of bolt 78. As such, when the electrode torque measurement apparatus is mounted on an electrode joining apparatus and the torque device engages a free electrode, load rod 64 is free to rotate about ball bearing 76 such that load rod 64 can be allowed to freely orient a force sensor attached to load rod 64 in a position wherein the force being applied on the force sensor by the torque device is applied in an axial direction with respect to the force sensor as opposed to at an angle with respect to the axis of the force sensor, which can help produce a more accurate torque calculation.

Thus, although there have been described particular embodiments of the present invention of a new and useful Electrode Torque Measurement Device, it is not intended that such references be construed as limitations upon the scope of this invention.

What is claimed is:

1. An electrode joining apparatus for joining a fixed electrode and a free electrode, comprising:
   an electrode holder configured to receive the fixed electrode;

a torque device positioned above the electrode holder, the torque device configured to grip and spin the free electrode to join the free electrode to the fixed electrode; and a force sensor coupled to the torque device, the torque device configured to apply a force on the force sensor when the torque device engages the free electrode, the force sensor configured to detect a signal representative of the force applied by the torque device on the free electrode.

2. The apparatus of claim 1, wherein the force sensor is a load cell.

3. The apparatus of claim 1, wherein the electrode holder is rotationally fixed.

4. The apparatus of claim 1, wherein the electrode holder is configured to grip the fixed electrode to prevent angular and axial movement of the fixed electrode.

5. The apparatus of claim 1, wherein the force sensor is coupled to the torque device and the electrode holder.

6. The apparatus of claim 1, further comprising a lift configured to vary the vertical position of the torque device.

7. The apparatus of claim 6, wherein the force sensor is coupled to the lift and the torque device.

8. The apparatus of claim 1, wherein the torque device is rotatable relative to the electrode holder, and the force sensor resists the rotation of the torque device to detect the signal representative of the force applied by the torque device on the free electrode.

9. The apparatus of claim 8, further comprising:
a base ring mounted to the electrode holder; and
a drive ring mounted to the torque device, the drive ring rotatably disposed on the base ring, the torque device rotatable relative to the electrode holder via the drive ring.

10. The apparatus of claim 9, further comprising a plurality of rollers disposed on the base ring, the rollers configured to accommodate the drive ring such that the drive ring is rotatable on the rollers.

11. The apparatus of claim 9, wherein:
the force sensor is coupled between the base ring and the drive ring;
the force sensor is coupled to the torque device via the drive ring; and
the torque device applies a force on the force sensor via the drive ring.

12. The apparatus of claim 8, further comprising a plurality of rollers disposed on the electrode holder, the torque device rotatable relative to the electrode holder via the plurality of rollers.

13. The apparatus of claim 1, wherein:
the torque device further comprises a control console;
the force sensor is configured to produce an electric voltage signal proportional to the force applied by the torque device on the free electrode; and
the force sensor communicates the electric voltage signal to the control console.

14. An electrode torque measurement apparatus for an electrode joining device, the electrode joining device including an electrode holder configured to receive a fixed electrode and a torque device configured to grip and spin a free electrode to join the free electrode to the fixed electrode, the apparatus comprising:
a base ring mountable to the electrode joining device;
a drive ring mountable to the torque device, the drive ring rotatable relative to the base ring; and
a force sensor coupled between the base ring and the drive ring, the torque device configured to apply a force on the force sensor via the drive ring when the base ring is mounted to the electrode joining device, the drive ring is mounted to the torque device, and the torque device engages the free electrode, the force sensor configured to detect a signal representative of the force applied by the torque device on the free electrode.

15. The apparatus of claim 14, further comprising a base flange protruding radially from the base ring, the force sensor coupled to the base ring via the base flange.

16. The apparatus of claim 14, further comprising a drive flange protruding radially from the drive ring, the force sensor coupled to the drive ring via the drive flange.

17. The apparatus of claim 14, further comprising a plurality of rollers located on the base ring, the plurality of rollers configured to accommodate the drive ring such that the drive ring is rotatable on the rollers.

18. The apparatus of claim 14, wherein the base ring is mountable to the electrode holder.

19. An electrode joining apparatus for joining a fixed electrode and a free electrode, comprising:
an electrode holder configured to receive the fixed electrode;
a torque device positioned above the electrode holder, the torque device configured to grip and spin the free electrode to join the free electrode to the fixed electrode;
an input indicator disposed on the torque device; and
an applied force sensor coupled to the torque device, the torque device configured to apply a force on the force sensor when the torque device engages the free electrode, the applied force sensor configured to detect a signal representative of the force applied by the torque device on the free electrode.

20. The apparatus of claim 19, wherein the torque device is configured to receive a hydraulic input, and the input indicator is a hydraulic pressure gauge.

* * * * *